(12) United States Patent
Zhang et al.

(10) Patent No.: US 7,942,817 B2
(45) Date of Patent: May 17, 2011

(54) PATIENT MONITORING AND TREATMENT MEDICAL SIGNAL INTERFACE SYSTEM

(75) Inventors: Hongxuan Zhang, Schaumburg, IL (US); Detlef W. Koertge, Carpentersville, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 85 days.

(21) Appl. No.: 12/330,948

(22) Filed: Dec. 9, 2008

(65) Prior Publication Data

US 2009/0177046 A1 Jul. 9, 2009

Related U.S. Application Data

(60) Provisional application No. 61/018,968, filed on Jan. 4, 2008.

(51) Int. Cl.
*A61B 5/00* (2006.01)
*A61B 5/04* (2006.01)
*A61N 1/37* (2006.01)

(52) U.S. Cl. ............ 600/300; 607/32; 607/60; 128/903; 128/904; 600/523

(58) Field of Classification Search ........................ None
See application file for complete search history.

(56) References Cited

U.S. PATENT DOCUMENTS

| | | | | |
|---|---|---|---|---|
| 4,742,831 A * | 5/1988 | Silvian | ........................ | 600/523 |
| 5,329,281 A * | 7/1994 | Baumgartner et al. | ....... | 341/139 |
| 5,474,090 A * | 12/1995 | Begun et al. | ................... | 600/520 |
| 5,941,906 A * | 8/1999 | Barreras et al. | ................. | 607/66 |
| 5,954,719 A | 9/1999 | Chen et al. | | |
| 6,018,677 A * | 1/2000 | Vidrine et al. | ................ | 600/520 |
| 6,037,840 A | 3/2000 | Myer | | |
| 6,302,844 B1 * | 10/2001 | Walker et al. | ................. | 600/300 |
| 6,346,104 B2 | 2/2002 | Daly et al. | | |
| 6,375,614 B1 * | 4/2002 | Braun et al. | ................. | 600/300 |
| 6,594,343 B1 | 7/2003 | Duffie et al. | | |
| 7,771,379 B2 * | 8/2010 | Treu | ......................... | 604/4.01 |
| 2006/0173364 A1 * | 8/2006 | Clancy et al. | ................. | 600/485 |

* cited by examiner

*Primary Examiner* — Eric F Winakur
*Assistant Examiner* — Bobby Soriano
(74) *Attorney, Agent, or Firm* — Alexander J Burke

(57) ABSTRACT

A medical signal interface device bidirectionally conveys signals between a patient and patient monitoring devices. The device comprises a bidirectional electrical signal interface that receives and buffers patient parameter monitoring signals received from a patient via patient attached leads and outputs treatment related signals used in applying invasive or non-invasive treatment to a patient. A bidirectional electrical signal processor operates in response to commands received from a control processor and is coupled to the electrical signal interface, for processing received patient parameter monitoring signals using filtering and amplification to provide processed patient monitoring signals for output to at least one patient monitoring device. The bidirectional electrical signal processor processes the treatment related signals for output by buffering the treatment related signals for output to a patient. A control processor provides data representing the commands in response to at least one of, (a) predetermined configuration data and (b) deriving data representing the commands from data entered by a user via a displayed user interface image.

18 Claims, 5 Drawing Sheets

PATIENT MONITORING AND TREATMENT MEDICAL SIGNAL INTERFACE SYSTEM

This is a non-provisional application of provisional application Ser. No. 61/018,968 filed Jan. 4, 2008, by H. Zhang et al.

FIELD OF THE INVENTION

This invention concerns a medical signal interface system intervening between a patient and patient monitoring devices for bidirectionally conveying signals including patient parameter monitoring signals received from a patient and treatment related signals used in applying invasive or non-invasive treatment to a patient.

BACKGROUND OF THE INVENTION

Patient signals, including electrophysiological (EP) and hemodynamic signals, are sensed and converted to electrical signals and data, such as surface ECG signals and intra-cardiac electrograms, which are monitored, processed, analyzed and stored by a computer system. Patient signals, such as ECG signals, are often distributed and shared between medical devices and systems using a signal splitter interface device. Typically known patient monitoring signal splitter interface devices are unidirectional and there is no direct electrical connection or leakage between different medical devices and systems, which limits degradation in signal quality and stability. Some known signal interface devices are used for signal transmission from patient to patient monitoring devices and some known interface devices are used for signal transmission from patient monitoring devices to a patient.

Known signal interface devices that concurrently transfer both patient signals (such as EP and Hemodynamic signals) and patient monitoring device signals (for test or patient treatment), are burdened by needing more cables and data connections. This increases system complexity and medical treatment procedure complexity and generates additional electrical noise and artifacts and risks reduction in patient safety particularly where signal acquisition and transmission catheters are attached to a patient heart, for example. Further, many medical electrical treatments involve additional cables and leads that are attached to patient anatomy such as for heart pacing stimulation and RF ablation treatment for cardiac arrhythmias. Additional cables are used for intra-cardiac catheters. Known signal interface devices fail to adequately support signal communication between a patient and monitoring and treatment devices whilst minimizing signal degradation and cabling complexity. A system according to invention principles addresses these deficiencies and related problems.

SUMMARY OF THE INVENTION

The inventors have advantageously recognized the need for a bidirectional signal interface device conveying signals including patient parameter monitoring signals received from a patient and treatment related signals used in applying invasive or non-invasive treatment to a patient. A system concurrently bidirectionally transfers patient signals (such as EP and Hemodynamic signals) and instrument signals (such as test stimulation and medical treatment signals) whilst supporting signal isolation and conditioning to provide accurate, reliable patient signal monitoring without introducing cabling complexity.

A medical signal interface device bidirectionally conveys signals between a patient and patient monitoring devices. The device comprises a bidirectional electrical signal interface that receives and buffers patient parameter monitoring signals received from a patient via patient attached leads and outputs treatment related signals used in applying invasive or non-invasive treatment to a patient. A bidirectional electrical signal processor operates in response to commands received from a control processor and is coupled to the electrical signal interface, for processing received patient parameter monitoring signals using filtering and amplification to provide processed patient monitoring signals for output to at least one patient monitoring device. The bidirectional electrical signal processor processes the treatment related signals for output by buffering the treatment related signals for output to a patient. A control processor provides data representing the commands in response to at least one of, (a) predetermined configuration data and (b) deriving data representing the commands from data entered by a user via a displayed user interface image.

DETAILED DESCRIPTION OF THE INVENTION

Figure 1:
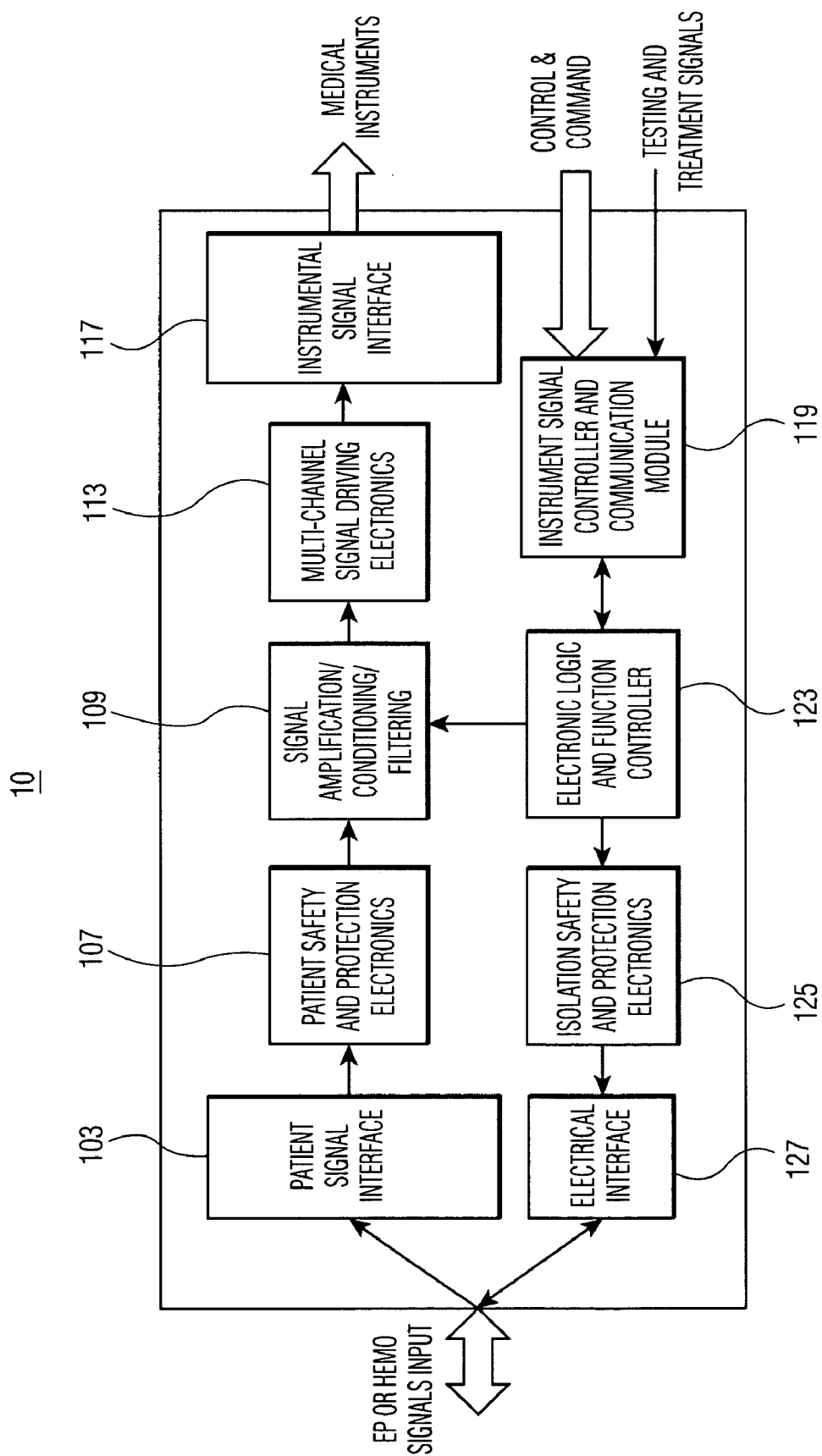
FIG. 1 shows a medical signal interface device for bidirectionally conveying signals between a patient and patient monitoring devices, according to invention principles.

Cardiac electrophysiological (EP) activity is sensed in the form of surface ECG signals and intra-cardiac electrograms and monitored and analyzed to identify cardiac arrhythmia and pathology related abnormality, for example. Usually cardiac signals from a patient are provided to different medical instruments, such as a signal monitoring system and an image data processing system, via a signal splitter and interface device. Typically test signals from one instrument conveyed via patient attached leads may cause noise and patient signal distortion in other instruments. Further, medical treatment signals conveyed from an instrument to a patient, supporting an ablation procedure, for example, may result in power (current and voltage) leakage, signal degradation and resultant safety impairment. Known medical signal interface devices typically fail to bidirectionally convey signals (e.g., electrophysiological signals) from a patient in one direction and test or treatment signals towards a patient in the opposite direction.

A medical signal interface device bidirectionally and concurrently conveys signals between a patient and patient monitoring devices including EP and Hemodynamic signals from a patient in one direction and testing stimulation and medical treatment signals towards a patient in the opposite direction. The medical signal interface device provides comprehensive signal isolation, signal conditioning and is versatile improving patient safety, efficiency and performance of medical treatment. The system supports patient signal transmission (to multiple medical instruments), signal connection testing and verification and also supports medical treatment. The versatile bidirectional medical signal interface device is programmable to automatically control automatic real time signal transmission and provides improved sensitivity, stability and reliability in support of a corresponding clinical application.

A processor as used herein is a device for executing stored machine-readable instructions for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example. A processor may be electrically coupled with any other processor enabling interaction and/or communication there-between. A processor comprising executable instructions may be electrically coupled by being within stored executable instruction enabling interaction and/or communication with executable instructions comprising another processor. A user interface processor or generator is a known element comprising electronic circuitry or software or a combination of both for generating display images or portions thereof. A user interface comprises one or more display images enabling user interaction with a processor or other device.

An executable application comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. An object or data object comprises a grouping of data, executable instructions or a combination of both or an executable procedure.

FIG. 1 shows medical signal interface device 10 for bidirectionally conveying signals between a patient and patient monitoring devices. The system addresses the deficiencies of known systems and improves performance of a signal interface and clinical procedure. System 10 bidirectionally transfers multi-channel signals, such as multi-channel patient (e.g., EP and Hemodynamic) signals, and multi-channel (e.g., multi-lead and sensor failure detection) test signals and treatment (e.g., multi-channel sequential pacing) signals. System 10 may integrate additional monitoring, analysis and clinical treatment related functions to reduce complexity and risk in a clinical procedure and treatment. Thereby system 10 may eliminate the need for an additional intra-cardiac (EP) catheter for cardiac pacing or ablation treatment, for example. System 10 electrically isolates and separates conveyed signals and employs conditioning and filtering to reduce signal noise and artifacts.

A signal pathway in medical signal interface device 10 is programmed and controlled via an electrical interface with a medical instrument or with a logic controlling circuit graphical user interface which increases clinical application flexibility and medical safety. System 10 is usable in an Intensive Care Unit (ICU) and Critical Care Unit (CCU) involving multi-functional instrument integration, including vital sign monitoring, ablation and hemodynamic signal monitoring, for example. Medical signal interface device 10 conveys patient signals to medical instruments (including imaging systems and patient monitoring systems) such as surface ECG signals, intra-cardiac EP signals, vital sign signals and Hemodynamic signals. Device 10 conveys signals to patients such as pacing treatment device external stimulation signals used in patient signal recording and monitoring, such as patient Motion Evoked Potential signals. Medical signal interface device 10 is programmable to control signal processing functions including bandwidth, filtering, and amplitude amplification to accommodate different kinds of patient signals having different characteristics. Device 10 controls processing logic and sequence of data processing and signal transmission.

FIG. 1 shows functional modules of medical signal interface device 10 including an electronic signal interface for conveying signals from patient to medical devices, an electronic signal interface for conveying signals from medical devices to a patient and a function logic and communication module for controlling device 10. A signal acquired from a patient is buffered by unit 103 and safety processed by unit 107 to provide safety isolation according to the IEC standards by using an isolation transformer or opto-isolator, for example. The signal is also protected with high voltage clamping circuitry to support data transmission. Unit 107 also minimizes leakage current to ground to minimize safety hazard. Further, amplification, conditioning and filter unit 109 amplifies, conditions and filters signals from unit 107 in response to configuration signals from controller and communication modules 119 and 123. Modules 119 and 123 control signal bandwidth and dynamic frequency range of data by controlling filter parameters and amplitude clamping threshold, signal conditioning and data transmission. Units 119 and 123 manage communication and command between medical signal interface device 10 and a user such as a patient monitoring computer or device user or a clinical user. Modules 119 and 123 provide flexibility, adaptive operational mode switching and efficiency in real time data processing, transmission steering and medical treatment.

The configuration signals provided by modules 119 and 123 dynamically configure amplification, processing and filtering based on signal feedback to ensure input signals of differing characteristics are appropriately conditioned. Multi-channel signal driver unit 113 processes amplified, conditioned and filtered signals from unit 109 to provide multi-channel signals (e.g., multiple ECG channel signals) to interface and communication unit 117 for communication to one or more different medical devices such as patient monitoring devices, an imaging (e.g., X-ray) system and an electronic patient record.

A treatment (or test) signal acquired from a treatment device or test unit is buffered within module 119 and is safety processed by unit 125, in a similar manner to unit 107, to provide safety isolation according to the IEC standards by using an isolation transformer or opto-isolator, for example. The treatment signal is high voltage clamped for safety. Unit 125 also minimizes leakage current to ground to minimize safety hazard in response to configuration signals from controller and communication module 119. Electrical interface 127 buffers and conditions signals from unit 125 for communication to a patient or for communication via patient attached leads (or internally in device 10) to unit 103 for closed loop signal path test of patient monitoring circuitry. The configuration signals provided by modules 119 and 123 dynamically configure treatment and test signal amplification, processing and filtering of units 119, 125 and 127.

Figure 2:
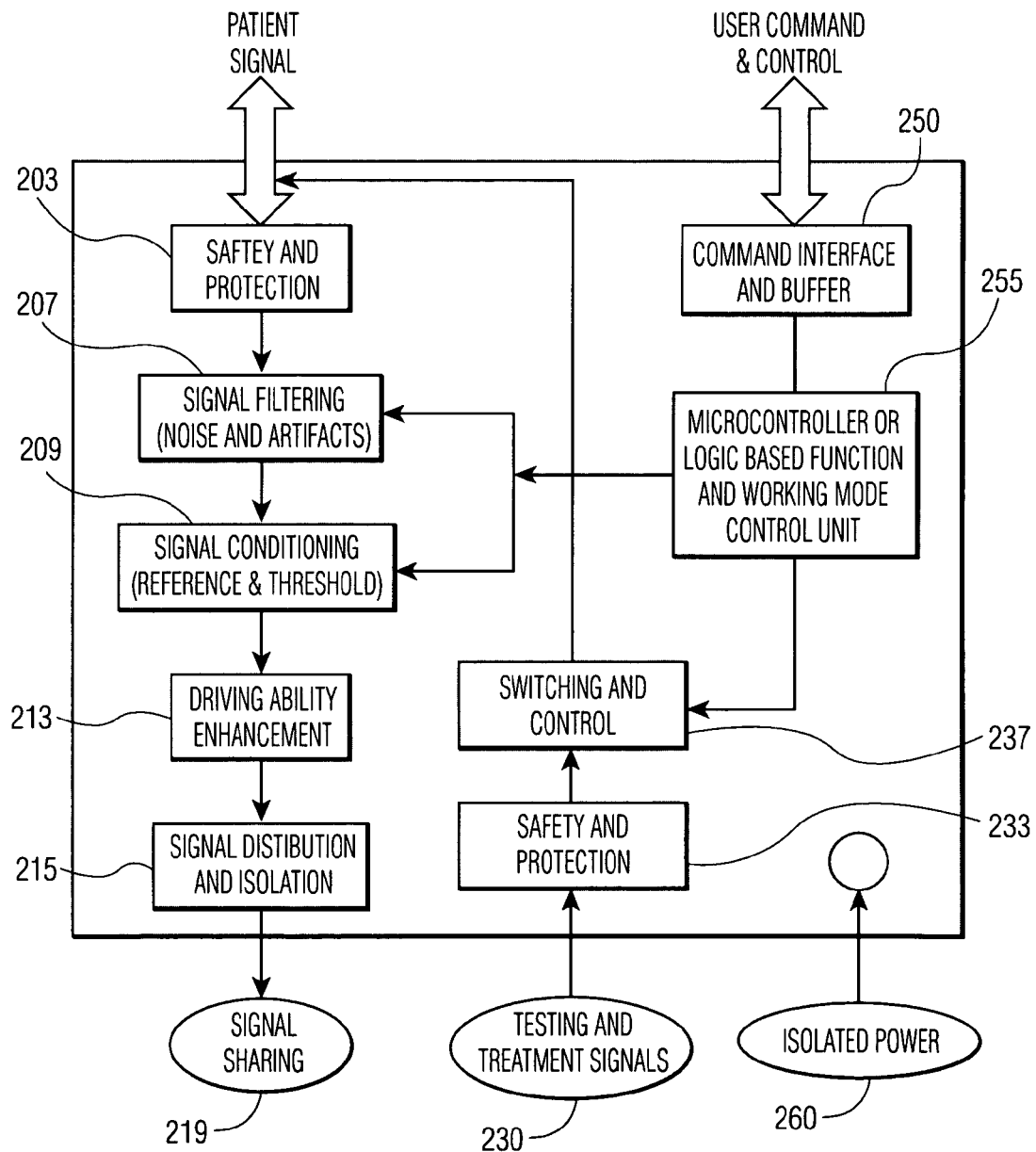
FIG. 2 shows a flowchart of operation of a medical signal interface device for bidirectionally conveying signals between a patient and patient monitoring devices, according to invention principles.

FIG. 2 shows a flowchart of operation of medical signal interface device 10 (FIG. 1) for bidirectionally conveying signals between a patient and patient monitoring devices. Unit 10 supports multiple concurrent processes including, signal conditioning and transmission, operation status control and function management. Function and processing flow is directed by command and communication interface and function controller 123 (FIG. 1) which may comprise a microcontroller or a logic device. Medical signal interface device 10 is powered by isolated medical power 260 and module 123 directs processing of parameters for patient signal conditioning and filtering as well as processing of treatment and testing signals, and signal channel switching. A signal acquired from a patient attached lead by interface 103 is safety processed by unit 107 in step 203 and filtered, conditioned and amplified by unit 109 in steps 207 and 209. Unit 113 in step 213 amplifies, conditions and filters signals to provide multi-channel signals (e.g., multiple ECG channel signals) for interface and isolated distribution (using isolated power) 260 by unit 117 in step 215 and signal sharing in step 219 to one or more different medical devices such as patient monitoring devices, an imaging (e.g., X-ray) system and an electronic patient record.

In step 230 a treatment (or test) signal acquired by unit 119 from a treatment device or test unit is buffered within module 119 and is safety processed by unit 125 in step 233. In step 237, electrical interface 127 buffers and conditions signals from unit 125 for communication to a patient or for communication via patient attached leads (or internally within device 10) for closed loop signal path test of patient monitoring circuitry. Electrical interface 127 also times signal switching on or off or switching between particular channels for test or patient treatment in response to control and configuration signals. The control and configuration signals are provided by modules 119 and 123 in step 255 based on command signals received from a medical device in step 250. The control and configuration signals adaptively configure medical signal interface device 10 for a particular clinical usage and application.

Figure 3:
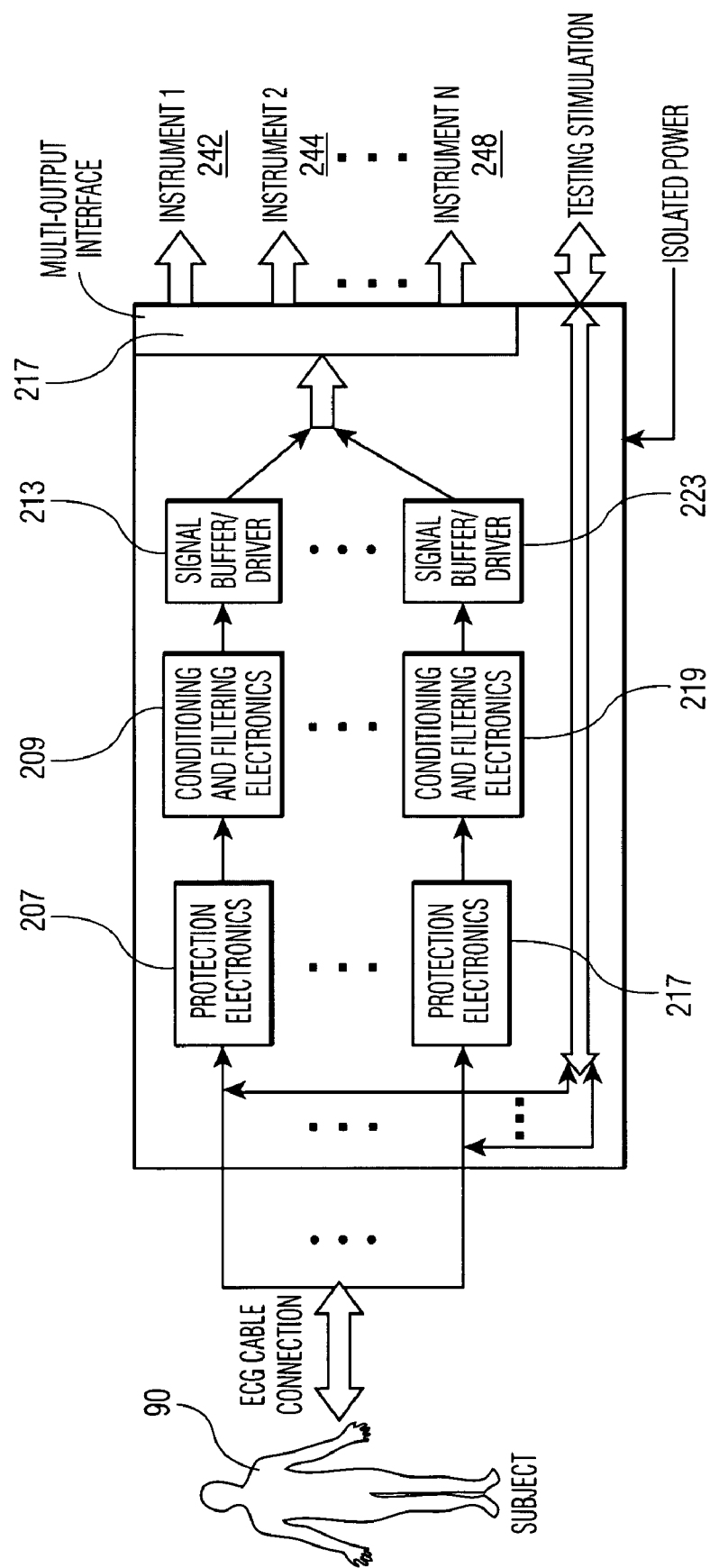
FIG. 3 shows a multi-channel output medical signal interface device for transferring ECG signals between a patient and a patient monitoring system or other medical instrumentation, according to invention principles.

FIG. 3 shows a multi-channel output medical signal interface device for transferring ECG signals between a patient and a patient monitoring system or other medical instrumentation and for lead failure detection. In some applications, a function and logic controller (e.g., controller 123 of FIG. 1) may not be utilized or needed such as in an application in which medical signal interface device 10 processes surface ECG signals for transmission and lead failure detection, for example. In such an ECG application medical signal interface device 10 supports functions including conditioning and distributing ECG signals to multiple medical instruments and provides test capability for monitoring and validating ECG lead and sensor connection status, such as lead failure or intermediate connection detection.

FIG. 3 illustrates operational flow of a medical signal interface device and mapping of bidirectional surface ECG signals by the device. In operation, N medical instruments (242, 244-248) receive surface ECG signals. The ECG signals at the output of the medical signal interface device are a combination of, (a) ECG lead signals from patient 90 and (b) fed back electrical test response signals from sensors and leads, $$out\_signal = ECG\_signal \oplus testing\_response$$

Typically, an AC test signal (for example, a 2 K Hz square wave) is employed as a stimulation test signals to measure ECG lead and sensor connection status. Test stimulation signals may be provided by a stimulation resource or from a medical instrument. Usually an ECG signal occupies a 0-250 Hz frequency bandwidth so there is negligible overlap and noise (artifact) introduced into ECG signals from test signals. For example, instrument 1 (unit 242) and 2 (unit 244) use ECG signals and comprise different image acquisition and processing systems produced by different manufacturers or are different products from a single manufacturer. Imaging systems 242 and 244 do not check surface ECG sensor and lead status and conditioning and filtering modules in these instruments eliminate the testing response signal. Instrument N (unit 248) is a patient signal recording system, which continuously monitors surface ECG lead status. The medical signal interface device communicates both an ECG signal and test response signal to instrument N (unit 248) enabling instrument N (unit 248) to continuously monitor surface ECG lead status. In another embodiment, test signals indicating ECG sensor and lead status are not communicated to specific instruments, specifically instruments 1 (unit 242) and 2 (unit 244) here. Signal conditioning and filter electronics in the medical signal interface device are adaptively configured in response to the system configuration data indicating types of different medical instruments and the clinical application being performed. The configuration data may be entered by a user or comprise predetermined configuration data or may be derived by auto-interrogation of attached devices by the medical signal interface device. In a further embodiment instruments 1-N may intermittently communicate configuration information to the medical signal interface device.

Individual ECG channel signals are processed by separate parallel processing paths, in this embodiment, for communication to N medical instruments (242, 244-248). Individual parallel processing paths comprise units 207, 209 and 213 in one path and units 217, 219 and 223 in another path, for example. Units 207 and 217 perform safety and signal protection processing on ECG lead signals eliminating high current and voltage spikes and energy leakage resulting from use of cardiac defibrillation, for example. Units 209 and 219 perform signal conditioning including signal amplification and frequency bandwidth adjustment to enhance signal quality. Units 213 and 223 comprise conditioned signal buffering, amplification and driving circuitry for providing signals to multiple output interface 217 for output to medical instruments (242, 244-248).

Figure 4:
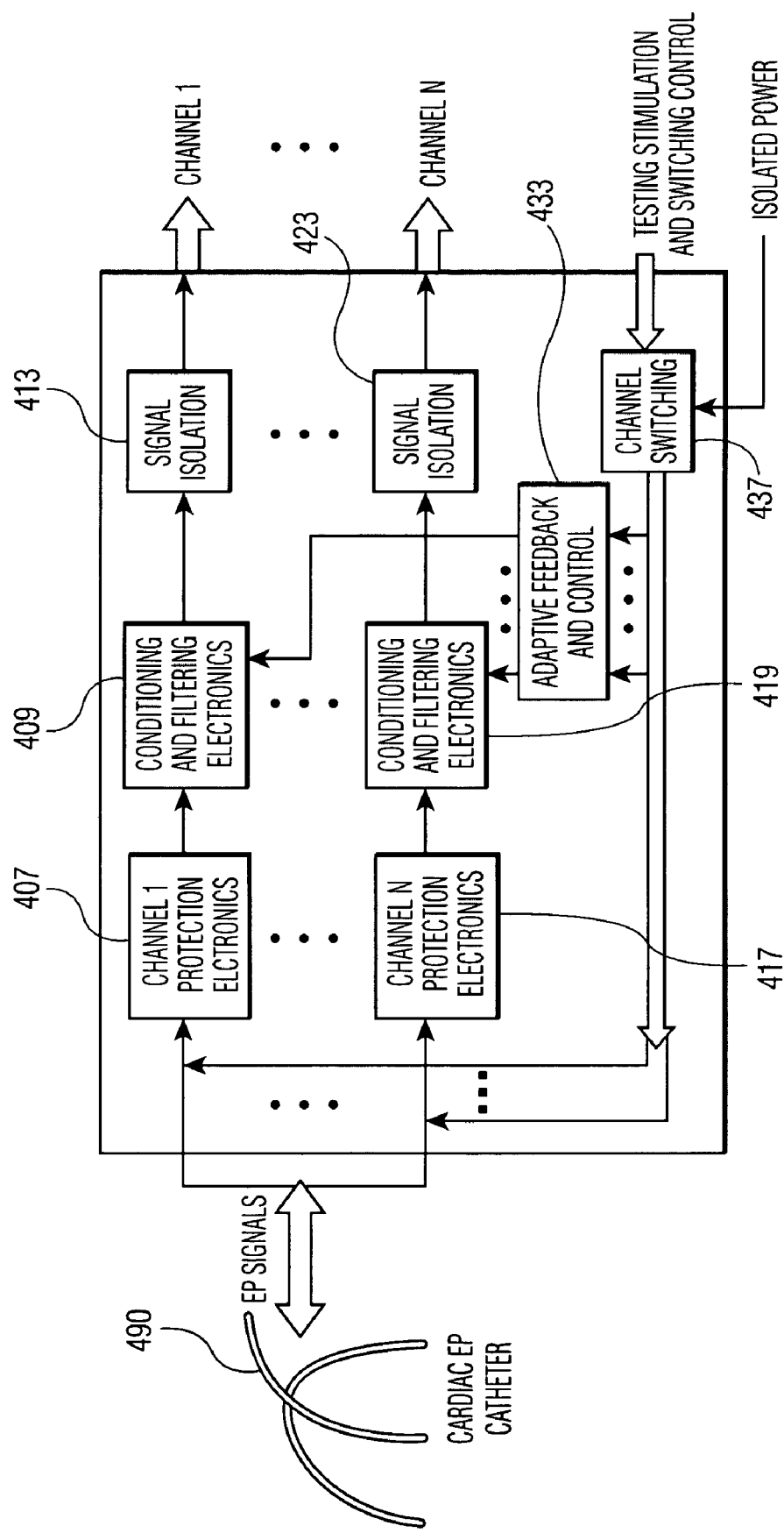
FIG. 4 shows an intra-cardiac medical signal interface device conveying EP signals and pacing stimulation signals and employing adaptive filtering and signal control, according to invention principles.

FIG. 4 shows a bidirectional intra-cardiac medical signal interface device conveying EP signals and pacing stimulation signals and employing adaptive filtering and signal control. Specifically, the system conveys intra-cardiac catheter treatment signals for stimulation, ablation or temperature control, for example. The intra-cardiac medical signal interface device couples output treatment signals to patient monitoring inputs for closed loop signal processing circuit testing. The intra-cardiac medical signal interface device is powered by an isolated power source and increases medical procedure efficiency and reduces complexity and risk of a treatment procedure. A cardiac pacing stimulation signal, for example, is usually coupled to an electrophysiological catheter and controlled with a complex switching strategy. Further, substantial signal noise is introduced (such as artifact tail effects, cross talk) and current leakage occurs since a pacing stimulation signal and EP signal are connected directly to patient anatomy. The bidirectional intra-cardiac medical signal interface device supports a pacing medical procedure and advantageously adaptively cancels pacing artifacts by adaptively adjusting pacing (or other treatment) signals via feedback through signal monitoring channels e.g., channel 1 comprising units 407, 409 and 413 to channel N comprising units 417, 419 and 423. The signal feedback is provided to a treatment medical instrument that adjusts the treatment signal in response to the feedback signal. Alternatively, treatment signal adjustment may be performed within the medical signal interface device in another embodiment. The medical signal interface device may similarly process other medical treatment signals, such as ablation signals for treating cardiac arrhythmias, for example.

Treatment (or test) signals from a treatment instrument are processed for communication on one or more channels by channel switch unit 437 and provided for output to EP cardiac catheter 490. The treatment (or test) signals are also provided to signal monitoring channels such as channel 1 comprising units 407, 409 and 413 to channel N comprising units 417, 419 and 423. Individual signal monitoring channels process signals in parallel processing paths. Units 407 and 417 perform safety and signal protection processing on signals eliminating high current and voltage spikes and energy leakage resulting from use of cardiac defibrillation, for example. Units 409 and 419 perform signal conditioning including signal amplification and frequency bandwidth adjustment to enhance signal quality. Units 413 and 423 provide signal isolation by using an isolation transformer or opto-isolator, for example and provide isolated output signals to medical instruments. Treatment signals from channel switch unit 437 are fed back through signal monitoring channels e.g., channel 1 comprising units 407, 409 and 413 to channel N comprising units 417, 419 and 423. The fed back signals are processed by the signal monitoring channels and provided to treatment instruments that use the processed signals to adaptively cancel noise and other artifacts in adaptively adjusting generated treatment signals provided to unit 437. Control unit 433 manages operation of the signal monitoring channels and the feedback noise cancellation process. The intra-cardiac medical signal interface device implements hardware (or software) based adaptive and programmable filtering and signal control in improving quality of treatment signals and reducing risk of the medical procedures.

Figure 5:
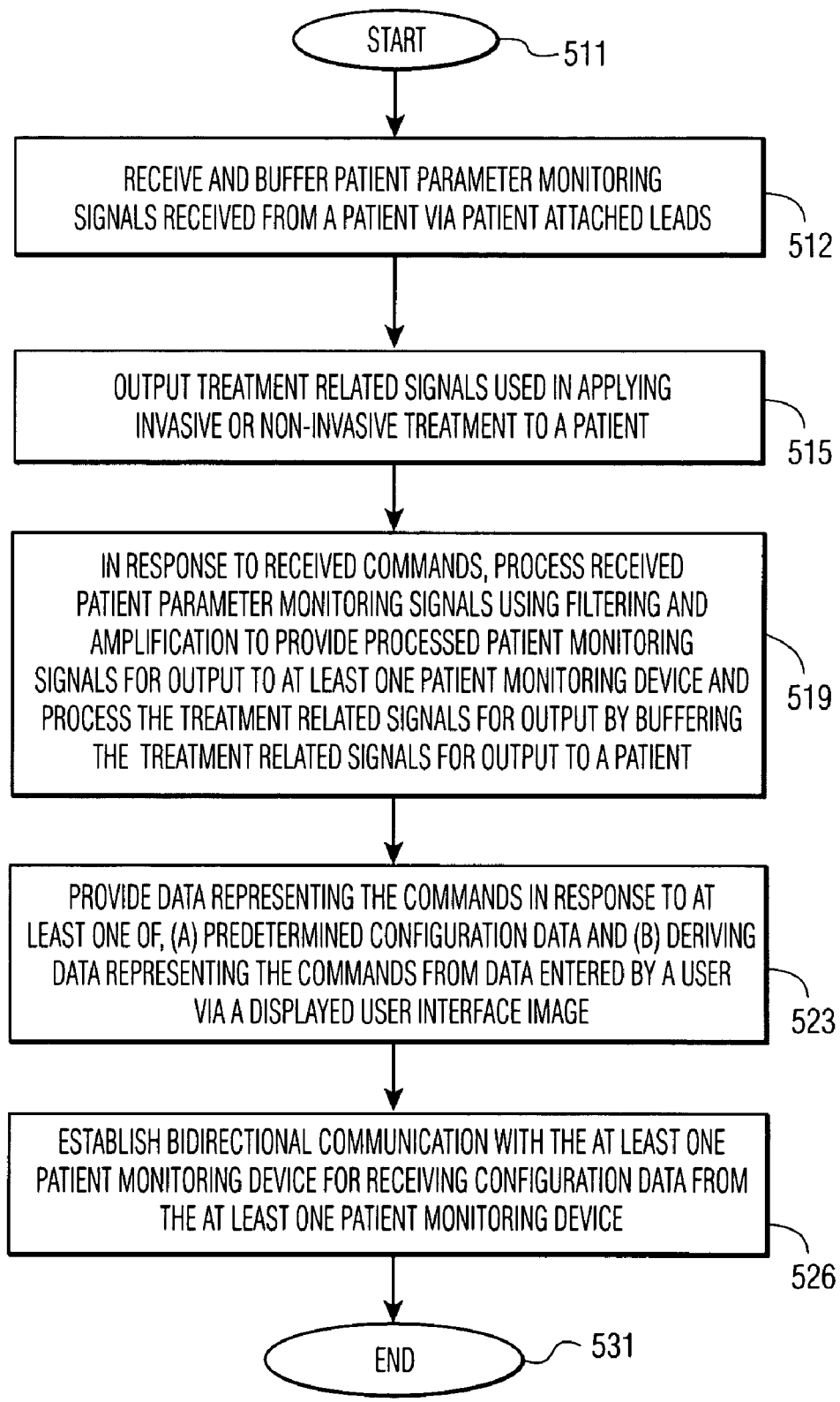
FIG. 5 shows a flowchart of a process used by a medical signal interface device for bidirectionally conveying signals between a patient and patient monitoring devices, according to invention principles.

FIG. 5 shows a flowchart of a process used by medical signal interface device 10 (FIG. 1) for bidirectionally conveying signals between a patient and patient monitoring devices. In step 512, following the start at step 511, system 10 receives and buffers patient parameter monitoring signals comprising analog signals received from a patient via patient attached leads. System 10 provides multiple different signal inputs for concurrently receiving and buffering patient parameter monitoring signals received from the patient and employs multiple processing channels for concurrently processing multiple received patient parameter monitoring signals to provide multiple processed patient monitoring signals for output to at least one patient monitoring device. System 10 receives, buffers and analog to digitally converts patient parameter monitoring signals received from a patient via patient attached leads.

System 10, in step 515, outputs treatment related signals used in applying invasive or non-invasive treatment to a patient. System 10 performs digital to analog conversion in concurrently outputting multiple treatment related signals used in applying invasive or non-invasive treatment to a patient. In step 519, in response to received commands, system 10 processes received patient parameter monitoring signals using filtering and amplification to provide processed patient monitoring signals for output to at least one patient monitoring device. System 10 further processes the treatment related signals for output by buffering the treatment related signals for output to a patient. The treatment related signals used in applying invasive or non-invasive treatment to the patient comprise a signal from a patient monitoring device to be applied to patient anatomy including at least one of, a heart pacing signal, an ablation signal and a stimulation signal, for example. The treatment related signals also include a test signal for testing an electrical connection and operation of patient monitoring circuitry. Further, the patient parameter monitoring signals received from the patient via patient attached leads comprise analog signals processed by a signal processing device and used in providing the treatment related signals to a patient in a closed loop.

A control processor (e.g., unit 123) in system 10 in step 523 provides data representing the commands in response to at least one of, (a) predetermined configuration data and (b) deriving data representing the commands from data entered by a user via a displayed user interface image. The control processor provides data representing commands for configuring at least one of a bidirectional electrical signal interface (e.g., units 103 and 127) and a bidirectional electrical signal processor (e.g., units 107, 109, 113, 125 and 119) in system 10 in response to configuration data received from at least one patient monitoring device.

A feedback processor (e.g., in unit 127) in system 10 selectively couples output treatment related signals to an input in system 10 for receiving and buffering patient parameter monitoring signals. The feedback processor selectively couples output treatment related signals to an input in the bidirectional electrical signal interface for receiving and buffering patient parameter monitoring signals to perform a closed loop test. Also the bidirectional electrical signal processor processes fed back output treatment related signals for use in adaptive noise cancellation. Processed fed back output treatment related signals are communicated to a medical treatment instrument for use in adaptive noise cancellation of generated treatment signals. In step 526, a communication processor in system 10 establishes bidirectional communication with the at least one patient monitoring device for receiving configuration data from the at least one patient monitoring device. The medical signal interface device automatically initiates interrogation of attached patient monitoring devices to acquire the configuration data from the at least one patient monitoring device. A bidirectional electrical signal interface and a bidirectional electrical signal processor in system 10, provide electrical isolation of signals provided to received from the patient. The process of FIG. 5 terminates at step 531.

The systems and processes of FIGS. 1-5 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. A bidirectional medical signal interface device operates in a closed-loop mode controlling treatment signals fed back to patients (sensing and controlling treatment directly or via a digital to analog converter) by manipulating patient monitoring device and/or treatment signal generation device operation to support closed loop treatment including a cyclic test, for example. Such a cyclic test varies patient treatment in accordance with a predetermined timed pattern and records resulting monitored patient medical parameters during the test. Further, the processes and applications may, in alternative embodiments, be located on one or more (e.g., distributed) processing devices. Any of the functions and steps provided in FIGS. 1-5 may be implemented in hardware, software or a combination of both.

What is claimed is:

1. A medical signal interface device for bidirectionally conveying signals between a patient and patient monitoring and treatment devices, comprising:
   a bidirectional electrical signal interface for,
      receiving and buffering patient parameter monitoring signals received from a patient via patient attached leads and
      concurrently outputting treatment related signals used in applying invasive or non-invasive treatment to a patient and providing electrical isolation of said patient parameter monitoring signals received from said patient via patient attached leads from treatment related signals used in applying invasive or non-invasive treatment output to a patient;
   a bidirectional electrical signal processor, responsive to commands received from a control processor and coupled to said electrical signal interface, for processing received patient parameter monitoring signals using filtering and amplification to provide processed patient monitoring signals for output to at least one patient monitoring device and for processing the treatment related signals for output by buffering the treatment related signals for output to a patient; and
   a control processor for providing data representing the commands in response to at least one of, (a) predetermined configuration data and (b) deriving data representing the commands from data entered by a user via a displayed user interface image.

2. A system according to claim 1, wherein
   said control processor adaptively configures said bidirectional electrical signal processor by providing data representing the commands, the commands being determined in response to data identifying said at least one patient monitoring device and
   said bidirectional electrical signal interface receives, buffers and analog to digitally converts patient parameter monitoring signals received from a patient via patient attached leads.

3. A system according to claim 2, wherein
   said control processor adaptively configures said bidirectional electrical signal processor by providing data representing the commands, the commands being determined in response to data identifying a device used in applying said invasive or non-invasive treatment to said patient and
   said bidirectional electrical signal interface performs digital to analog conversion in providing said treatment related signals used in applying invasive or non-invasive treatment to said patient.

4. A system according to claim 1, wherein
   said bidirectional electrical signal processor, provide electrical isolation of signals provided to, and received from, said patient
   said bidirectional electrical signal interface provides separate isolated safety protection processing of,
      (a) said patient parameter monitoring signals received from said patient via patient attached leads and
      (b) treatment related signals used in applying invasive or non-invasive treatment output to a patient.

5. A system according to claim 4, wherein
   said separate isolated safety protection processing comprises voltage clamping.

6. A system according to claim 1, wherein
   said bidirectional electrical signal interface provides a plurality of different signal inputs for concurrently receiving and buffering patient parameter monitoring signals received from said patient and
   said bidirectional electrical signal processor employs a plurality of processing channels for concurrently processing a plurality of received patient parameter monitoring signals to provide a plurality of processed patient monitoring signals for output to at least one patient monitoring device.

7. A system according to claim 6, wherein
   said bidirectional electrical signal processor concurrently outputs a plurality of treatment related signals used in applying invasive or non-invasive treatment to a patient.

8. A system according to claim 1, wherein
   said control processor provides data representing commands for configuring at least one of said bidirectional electrical signal interface and said bidirectional electrical signal processor in response to configuration data received from at least one patient monitoring device.

9. A system according to claim 8, including
   a communication processor for establishing bidirectional communication with said at least one patient monitoring device for receiving configuration data from said at least one patient monitoring device.

10. A system according to claim 9, wherein
    said medical signal interface device automatically initiates interrogation of attached patient monitoring devices to acquire said configuration data from said at least one patient monitoring device.

11. A system according to claim 1, wherein
    said patient parameter monitoring signals received from said patient via patient attached leads comprise analog signals and
    said treatment related signals used in applying invasive or non-invasive treatment to said patient comprise a signal from a patient monitoring device to be applied to patient anatomy including at least one of, a heart pacing signal, an ablation signal, a stimulation signal.

12. A system according to claim 11, wherein
said treatment related signals include a test signal for testing an electrical connection and operation of patient monitoring circuitry.

13. A system according to claim 1, wherein
said patient parameter monitoring signals received from said patient via patient attached leads comprise analog signals processed by a signal processing device and used in providing said treatment related signals to a patient in a closed loop.

14. A medical signal interface device for bidirectionally conveying signals between a patient and patient monitoring and treatment devices, comprising:
a bidirectional electrical signal interface for,
receiving and buffering patient parameter monitoring signals received from a patient via patient attached leads and
outputting treatment related signals used in applying invasive or non-invasive treatment to a patient and providing electrical isolation of said patient parameter monitoring signals received from said patient via patient attached leads from treatment related signals used in applying invasive or non-invasive treatment output to a patient;
a bidirectional electrical signal processor, responsive to commands received from a control processor and coupled to said electrical signal interface, for processing received patient parameter monitoring signals using filtering and amplification to provide processed patient monitoring signals for output to at least one patient monitoring device and for processing the treatment related signals for output by buffering the treatment related signals for output to a patient;
a feedback processor for selectively coupling output treatment related signals to an input in the bidirectional electrical signal interface for receiving and buffering patient parameter monitoring signals; and
a control processor for providing data representing the commands in response to at least one of, (a) predetermined configuration data and (b) deriving data representing the commands from data entered by a user via a displayed user interface image, said control processor adaptively configures said bidirectional electrical signal processor by providing data representing the commands, the commands being determined in response to data identifying at least one of, said at least one patient monitoring device and a device used in applying said invasive or non-invasive treatment to said patient.

15. A system according to claim 14, wherein
said feedback processor selectively couples output treatment related signals to an input in the bidirectional electrical signal interface for receiving and buffering patient parameter monitoring signals to perform a closed loop test.

16. A system according to claim 14, wherein
said bidirectional electrical signal processor processes fed back output treatment related signals for use in adaptive noise cancellation.

17. A system according to claim 16, wherein
the processed fed back output treatment related signals are communicated to a medical treatment instrument for use in adaptive noise cancellation of generated treatment signals.

18. A method employed by a medical signal interface device for bidirectionally conveying signals between a patient and patient monitoring and treatment devices, comprising the activities of:
receiving and buffering patient parameter monitoring signals received from a patient via patient attached leads;
outputting treatment related signals used in applying invasive or non-invasive treatment to a patient;
providing electrical isolation of said patient parameter monitoring signals received from said patient via patient attached leads from treatment related signals used in applying invasive or non-invasive treatment output to a patient;
in response to received commands,
processing received patient parameter monitoring signals using filtering and amplification to provide processed patient monitoring signals for output to at least one patient monitoring device and
processing the treatment related signals for output by buffering the treatment related signals for output to a patient; and
providing data representing the commands in response to at least one of, (a) predetermined configuration data and (b) deriving data representing the commands from data entered by a user via a displayed user interface image.

* * * * *